United States Patent [19]

Liesch et al.

[11] Patent Number: 5,756,472
[45] Date of Patent: May 26, 1998

[54] ANTIFUNGAL AGENT OBTAINED FROM HORMONEMA

[75] Inventors: Jerrold M. Liesch, Princeton Junction; Maria S. Meinz, Fair Haven; Janet C. Onishi; Sandra A. Morris, both of Westfield; Robert E. Schwartz, Scotch Plains; Gerald F. Bills, Clark; Robert A. Giacobbe, Lavallette; Wendy S. Horn, Westfield; Deborah L. Zink, Manalapan, all of N.J.; Angeles Cabello, Madrid, Spain; Maria T. Diez, Madrid, Spain; Isabella Martin, Madrid, Spain; Fernando Pelaez, Madrid, Spain; Francisca Vicente, Madrid, Spain

[73] Assignee: Merck & Co., Inc., Rahway, N.J.

[21] Appl. No.: 789,349

[22] Filed: Jan. 27, 1997

Related U.S. Application Data

[60] Provisional application No. 60/010,934 Jan. 31, 1996.

[51] Int. Cl.[6] ............................ A61K 31/70; C12N 1/14; C07D 315/00
[52] U.S. Cl. ............................ 514/27; 435/53; 435/254.1; 435/911; 549/415
[58] Field of Search ...................... 435/53, 254.1, 435/911; 514/27; 549/415

[56] References Cited

PUBLICATIONS

De Hoog et al., Mycology, 15:178–222, 1977.
Hermanides–Nijhof, Mycology, 15:141–177, 1977.

*Primary Examiner*—Michael G. Wityshyn
*Assistant Examiner*—Janet M. Kerr
*Attorney, Agent, or Firm*—Elliott Korsen; Mark R. Daniel

[57] ABSTRACT

There is disclosed a novel compound having the formula

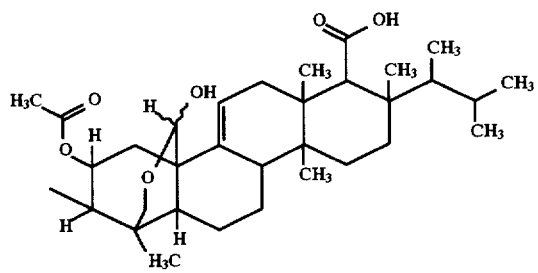

which exhibits antifungal activity.

5 Claims, 1 Drawing Sheet

ANTIFUNGAL AGENT OBTAINED FROM HORMONEMA

This application claims the benefit of U.S. Provisional application Ser. No. 60/010,934, filed Jan. 31, 1996.

The present invention relates to a novel antifungal compound, compositions containing said compound and methods of use. The compound and compositions exhibit broad spectrum antifungal activity against human fungal pathogens.

Clinical treatment of human fungal infections has relied mainly on two types of antifungal agents. These agents are amphotericin B, flucytosine and nystatin, which are fungicidal and capable of curing fungal infections at the cost of severe side effects to the patient, and fluconazole and other azole agents, which exhibit fewer side effects but are only fungistatic.

Thus, there is a need for new human antifungal agents.

SUMMARY OF THE INVENTION

The compound of the invention is a mixture of two diastereomers which are capable of being separated but reequilibrate at normal temperatures. The mixture will be shown as compound I below:

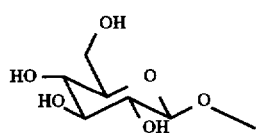

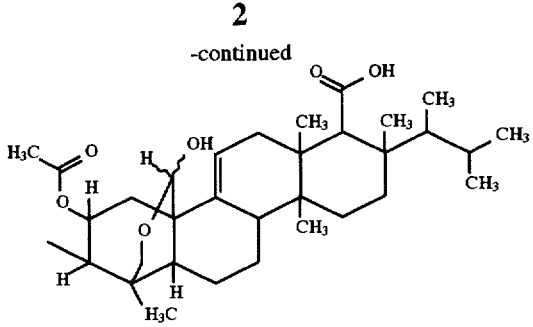

(I)

The structures of the two forms (Ia) and (Ib) are shown below:

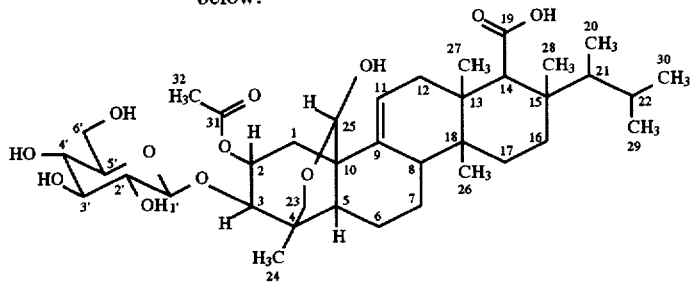

(Ia)

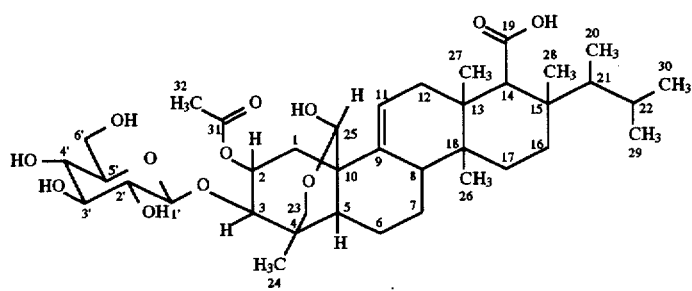

(Ib)

The compound has antimicrobial and fungicidal properties and may be useful for controlling systemic and superficial fungal infections in humans with fewer side effects than standard antifungal agents such as amphotericin B or fluconazole.

The compound is obtained by cultivation of a strain of an endophytic fungus, Hormonema sp., MF 6176, in the culture collection of Merck & Co., Inc., Rahway, N.J.

The characterization of the compound will include NMR data on each form while the biological activity will show results for the mixture of the diastereomers.

DETAILED DESCRIPTION OF THE INVENTION

Figure 1:
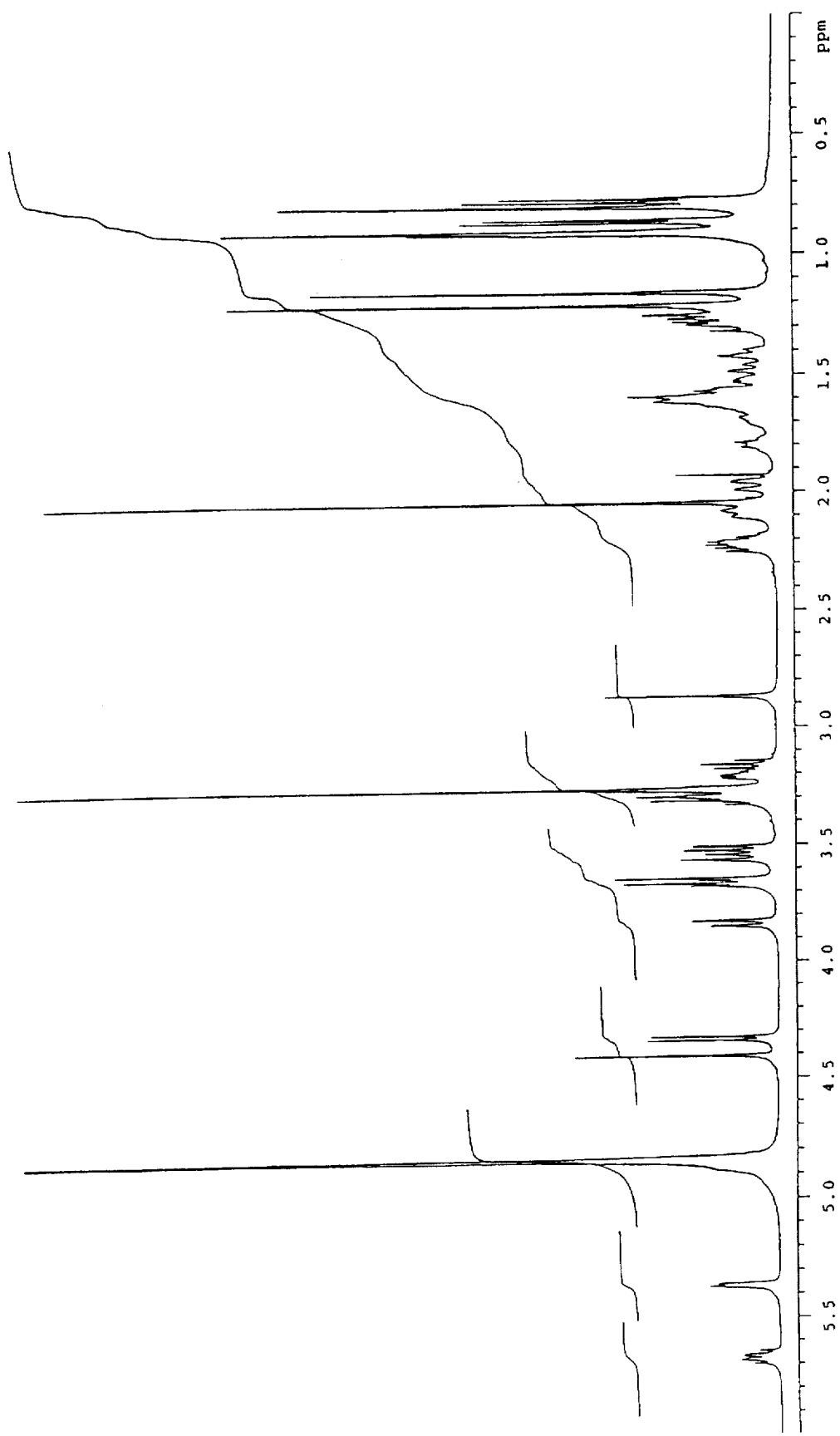
FIG. 1 is a proton nuclear magnetic resonance spectrum for Compound I. The compound exists naturally as two interconverting diastereomers. The peak shown at approximately 3.30 ppm represents the solvent, $CD_3OD$.

The compound is white and characterized by the following spectral properties:

Infrared Special Data

Recorded as a thin film on ZnSe: 3406 br, 1708 $cm^{-1}$

Mass Spectral Data

Mass spectra were recorded on a JEOL HX110 (Fast Atom Bombardment, FAB) mass spectrometer using a matrix of dithiothreitol-dithioerythritol (20/80). The exact mass measurements were made at high resolution with Ultramark™ 1960 (Fomblin) as the reference compound.

HR FAB-MS Found for $C_{38}H_{60}O_{12}$+Na: 731.4083

Calculated for $C_{38}H_{60}O_{12}$+Na: 731.3982

NMR Spectral Data

NMR spectra were recorded in $CD_3OD$ at 500 MHz ($^1H$) or 125 MHz ($^{13}C$). Chemical shifts are reported downfield from TMS (tetramethylsilane) and spectra were referenced to the solvent peak (3.30 ppm for $^1H$ spectra and 49.0 ppm for $^{13}C$ spectra).

$^1H$ NMR Spectra

The $^1H$ NMR spectrum of Compounds Ia and Ib is seen in FIG. 1. The $^1H$ NMR spectrum was recorded in $CD_3OD$ (0.15 ml) at 500 MHz on a Varian Unity 500 spectrometer at 25° C. Chemical shifts are given in ppm relative to tetramethylsilane (TMS) at zero ppm and referenced to the internal solvent peak at 3.30 ppm.

$^{13}C$ NMR Spectra (Major diastereomer)

$^{13}C$: δ 8.4(q), 16.1(q), 17.2(q), 17.5(q), 18.9(q), 19.4(t), 20.9(t), 21.2(q), 21.7(q), 25.3(q), 27.7(d), 29.0(t), 30.0(t), 38.5(s), 38.6(t), 39.0(s), 39.8(t), 41.2(d), 41.3(s), 41.5(d), 41.7(s), 45.3(s), 49.1(d), 53.4(d), 62.9(t), 66.1(t), 71.8(d), 74.4(d), 75.7(d), 77.8(d), 78.1(d), 87.8(d), 97.2(d), 105.3(d), 125.1(d), 140.3(s), 173.3(s), 177.6(s) ppm (Minor diastereomer)

$^{13}C$: δ 8.4(q), 16.5(q), 17.0(q), 18.2(q), 18.9(q), 18.8(t), 21.5(t), 21.2(q), 21.6(q), 25.3(q), 27.7(d), 29.3(t), 30.0(t), 38.5(s), 39.0(t), 38.8(s), 45.4(t), 38.8(d), 40.9(s), 40.1(d), 41.7(s), 43.5(s), 49.1(d), 53.6(d), 62.8(t), 59.7(t), 71.7(d), 74.8(d), 75.8(d), 77.7(d), 78.2(d), 88.0(d), 98.8(d), 105.3(d), 120.0(d), 144.1(s), 173.2(s), 177.7(s) ppm The compound of this invention has antimicrobial properties and is especially useful as an antifungal agent against both filamentous fungi and yeasts. It is useful against organisms causing systemic human pathogenic mycotic infections such as *Candida albicans, Candida tropicalis, Candida guillermondii, Candida glabrata, Aspergillus fumigatus, Candida pseudotropicalis, Saccharomyces cerevisiae, Aspergillus flavus* et al. It is also useful against organisms causing superficial fungal infections such as Trichoderma sp. and Candida sp. These properties may be effectively utilized by administering compositions containing an antifungal amount of the compound to an area, object or subject, on or in which fungi are to be controlled. Thus, compositions containing an antifungally effective amount of the compound and their use for the control of fungi are aspects of the present invention. An especially preferred aspect of the present invention are compositions in a pharmaceutically acceptable carrier and their use for the control of mycotic infections by administering a therapeutically effective amount of the compound.

The compound of the present invention is a natural product produced from a strain of Hormonema, MF 6176 in the culture collection of Merck & Co., Inc., Rahway, N.J., which has been deposited under the Budapest Treaty in the culture collection of the American Type Culture Collection on Jan. 23, 1996 at 12301 Parklawn Drive, Rockville, Md. 20852 and assigned accession number ATCC 74360.

The producing fungus is a Hormonema sp. (MF 6176, ATCC 74360) that was isolated from living leaves of an unidentified shrub collected in Navalquejigo, province of Madrid, Spain.

In agar culture, colonies of the fungus exhibit the following morphology:

Colonies on YM agar (Difco) at 25° C., 12 hr photoperiod growing slowly, attaining 20–24 mm in 21 days, raised, moist, mucoid to waxy at the center, but becoming velvety towards the margin, with margin submerged, even to undulating, with some radial plications or radial sectors, sectors may alternate between predominantly mycelium or yeast-like conidia, azonate, translucent at the margin but soon dark olivaceous gray to nearly black. Dark Olive Gray, Olivaceous Black, Blackish Green Gray (capitalized color names from Ridgway, R. 1912 Color Standards and Nomenclature. Published by the author, Washington, D.C.), reverse similar in color, without odors or exudates. No growth on YM at 37° C.

Colonies on Spezieller Nährstoffarmer agar (D. Brayford. 1992. In Methods for Research on Soilborne Phytopathogenic Fungi. Edited by L. L. Singleton, J. D. Mihail & C. M. Rush. American Phytopathological Society Press, St. Paul, Minnesota. pp. 103–106) at 25° C., 12 hr photoperiod, growing very slowly, attaining 17–18 mm in 21 days, with advancing zone submerged to appressed, undulating, aerial mycelium absent, azonate, at first forming constricted black to dark olive gray mucoid, radial strands due to predominance of yeast-like conidia, but with maturation colony becomes predominantly mycelial, with mycelial zones pale olive gray, Storm Gray, Light Olive-Gray, to translucent at advancing margin, reverse similar in color, exudates and odors absent.

Colonies on cornmeal agar (Difco) at 25° C., 12 hr photoperiod, growing slowly attaining 10–17 mm in 21 days, submerged to appressed at the margin, raised and mucoid towards the center, aerial mycelium absent, translucent olivaceous black to black, reverse similar in color.

Conidiophores absent. Conidiogenous cells holoblastic, integrated, intercalary, usually not differentiated from main axes of vegetative mycelium, occasionally arising from an undifferentiated lateral cell or filament. Conidia up to 14.5 μm long, up to 3.5 μm wide, aseptate, usually ellipsoidal with tapered apex and base, but quite variable, occasionally pyriform or subglobose, smooth, often with one or more budding scars, hyaline to pale olivaceous gray, often budding to produce 1 or 2 secondary conidia, accumulating in yeast-like masses along radial axes of vegetative hyphae. Mycelium consisting of contorted, wide, often thick-walled, hyaline to dematiaceous, short-cylindrical to subglobose cells, often with hyphal cells longitudinally septate, with individual cells up to 18 μm in diameter.

MF 6176 is assigned to the anamorph genus Hormonema based on filamentous mycelium composed of wide, dematiaceous hyphae that do not separate into arthrospores, absence of undifferentiated conidiophores, conidiogenous cells with basipetal conidiogenesis, and conidia that produce abundant secondary budding (G. S. De Hoog & E. J. Hermanides-Nijhof. 1977. Survey of the black yeasts and allied fungi. Centraalbureau voor Schimmelcultures Studies in Mycology 15: 178–222). MF 6176, with its slow radial growth and large conidia, is most similar to a group of unnamed Hormonema species which are anamorphs of plant-inhabiting loculoascomycetes (E. J. Hermanides-Nijhof. 1977. Auerobasidium and allied genera. Centraalbureau voor Schimmelcultures Studies in Mycology 15: 141–177).

Although the invention is discussed principally with respect to the specific strain, it is well known in the art that the properties of microorganisms can be varied naturally and artificially. Thus, all strains derived from Hormonema sp. MF 6176, ATCC 74360 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

The production of the compound may be carried out by cultivating the Hormonema sp. MF 6176, ATCC 74360 in a suitable nutrient medium, under conditions described herein, until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate the compound from other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as rice, oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium. These, however, are merely illustrative of the wide variety of media which may be employed and are not intended to be limiting.

TABLE 1

| KF SEED MEDIUM | | Trace Element Mix | |
|---|---|---|---|
| | per liter | | per liter |
| Corn Steep Liquor | 5 g | FeSO$_4$.7 H$_2$O | 1 g |
| Tomato Paste | 40 g | MnSO$_4$.4 H$_2$O | 1 g |
| Oat flour | 10 g | CuCl$_2$.2 H$_2$O | 25 mg |
| Glucose | 10 g | CaCl$_2$ | 100 mg |
| Trace Element Mix | 10 ml | H$_3$BO$_3$ | 56 mg |
| | | (NH$_4$)$_6$Mo$_7$O$_{24}$.4 H$_2$O | 19 mg |
| pH = 6.8 | | ZnSO$_4$.7 H$_2$O | 200 mg |

TABLE 2

SOLID PRODUCTION MEDIUM

| Component | per 250 ml flask |
|---|---|
| Brown Rice | 10 g |
| Yeast Extract | 20 mg |
| Sodium Tartrate | 10 mg |
| KH$_2$PO$_4$ | 10 mg |
| Distilled Water | 20 ml | pH was not adjusted prior to autoclaving for 20 minutes. Immediately before use, the medium was moistened with 15 ml of distilled water and autoclaved again for 20 minutes.

TABLE 3

LIQUID PRODUCTION MEDIUM

| Component | per liter |
|---|---|
| Glucose | 50 g |
| Tryptophan | 1 g |
| Fidco-Yeast Extract | 10 g |
| NZ-Amine (type E) | 33 g |
| Ammonium Sulfate | 5 g |
| KH$_2$PO$_4$ | 9 g | pH adjusted to 6.2 with NaOH before autoclaving.

Of the foregoing media, the solid production medium was found to give the best yield of the compound. In the production of the compound, generally, the culture is first grown in a seed medium and the culture growth then used to inoculate a production medium. The production medium may be a solid medium or a liquid medium.

In carrying out the production of Compound I, vegetative mycelia of the culture were prepared by inoculating 54 ml of seed medium (Table 1) in a 250 ml unbaffled Erlenmeyer flask with 2 ml of mycelia in 10% glycerol that had been stored at −80° C. Seed cultures were incubated for 3 days at 25° C. and 85% relative humidity on a rotary shaker with a 5-cm throw at 220 rpm in a room with constant fluorescent light. 2 ml portions of the culture were used to inoculate a second stage seed culture and further incubated for 3 days with the conditions noted above. 2 ml portions of this 3 day culture were used to inoculate 50 ml portions of the liquid production medium (Table 3) or solid rice-based production medium (Table 2) in 250 ml unbaffled Erlenmeyer flasks.

The usefulness of the compound as an antifungal agent, especially as an antimycotic agent, may be demonstrated with the compound in a broth microdilution assay for the determination of minimum inhibitory concentration (MIC) and minimum fungicidal concentration (MFC) against fungi. The compound is found to be effective in the assay against a panel of fungi selected for their resistance/susceptibility to known compounds, animal virulence, source and clinical importance, at concentrations comparable to an established antifungal agent, amphotericin B.

In the microbroth dilution assay, microorganisms were selected by streaking a yeast culture on Sabouraud dextrose agar (SDA) and incubating for 24–48 hours at 35°–37° C. Three to five characteristic colonies were selected and transferred to a fresh plate and incubated under similar conditions. From the regrowth, 3 to 5 colonies were selected and suspended in 10 milliliters of YM broth (Difco) and incubated for 4 hours at 35°–37° C. shaking at 225 rpm. The 4 hour broth cultures were adjusted optically to 86% transmission resulting in a concentration of $1-5 \times 10^6$ cfu/ml which was further diluted 1:100 in YNBD (yeast nitrogen base with 1% dextrose) to obtain a concentration of $1-5 \times 10^4$ cfu/ml for use as inocula.

The test compound was dissolved at 256 µg/ml in 10% DMSO and diluted 2× into the first well to achieve a concentration of 256 µg/ml at 5% DMSO in the first well. Compounds are subsequently serially diluted 2× and cell suspension is added to each well resulting in an additional 2× dilution of compound. 75 µl of said solution is delivered to each well in column 1 of a 96-well, U-bottomed plate. The compounds in column 1 were then serially diluted two-fold to yield concentrations from 128 µg/ml to 0.03 µg/ml.

Amphotericin B, the control compound, was prepared as a stock solution of 256 µg/ml in 10% DMSO and 75 µl of said solution delivered to column 1 of a 96-well, U-bottomed plate. The compounds in column 1 were then serially diluted two-fold to yield concentrations from 128 µg/ml to 0.06 µg/ml.

The plates containing the diluted compounds were then inoculated with 75 µl/well of the appropriate microorganism and incubated for 48 hours at 35°–37° C. with MIC (minimum inhibitory concentration) determinations carried out after 24 hours of incubation (except Cryptococcus strains which are read at 48 hours). Growth and sterility controls for each organism and sterility checks for the compounds also were carried out.

After recording MICs at 24 hours, the microtiter plates were shaken gently to resuspend the cells. A 1.5 µl sample was transferred from each well of the 96-well plate to a single reservoir inoculum plate containing SDA. The inoculated SDA and corresponding microtiter plates were incubated for 24 hours at 35°–37° C. For *Cryptococcus neoformans*, SDA plates were inoculated at 48 hours after recording MICs and incubated 48 hours before reading the MFC. MFC is the lowest concentration of compound at which either no growth or growth of <4 colonies occur.

No MFC values are indicated for *Aspergillus fumigatus* since colony counts are unreliable with filamentous species. Instead, a Minimum Effective Concentration (MEC) is reported. The MEC is defined as the lowest concentration of drug which effects a severe morphological change in the cells. The MEC is scored macroscopically by direct observation of the plate wells after 24 hours and reflects microscopic alterations in cell morphology (Kurtz et al, AAC 1994 38:1480–1489).

Minimum Fungicidal Concentration (MFC)

Minimum Inhibitory Concentration (MIC)

µg/ml

| Strain | MIC | MFC | MEC |
|---|---|---|---|
| Candida albicans (MY1055) | 0.5 | 0.25 | |
| Candida glabrata (MY1381) | 1.0 | 0.5 | |
| Candida parapsilosis (MY1010) | 0.25 | 0.25 | |
| Candida pseudotropicalis (MY2099) | 0.5 | 1.0 | |
| Candida tropicalis (MY1124) | 16.0 | 16.0 | |
| Candida albicans (CLY539) | 0.5 | 0.5 | |
| Candida albicans (CA2) | >128.0 | >128.0 | |
| Candida tropicalis (MY1012) | 1.0 | 1.0 | |
| Candida guillermondii (MY1019) | 1.0 | 2.0 | |
| Candida krusei | 4.0 | 1.0 | |
| Cryptococcus neoformans (MY2061) | 32.0 | 32.0 | |

-continued

| Strain | MIC | MFC | MEC |
|---|---|---|---|
| Cryptococcus neoformans (MY2062) | 32.0 | 128.0 | |
| Saccharomyces cerevisiae (MY2140) | 2.0 | 2.0 | |
| Aspergillus fumigatus (MY4839) | 64.0 | | 0.031 |
| Aspergillus fumigatus (MY5668) | 32.0 | | 0.031 |

The compound is also useful for inhibiting the growth of filamentous fungi. Such use may be illustrated in the following tests with *Aspergillus flavus, Fusarium oxysporum, Ustilago zeae* and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied directly to the agar plates as methanol solutions. When the sample to be tested is crude broth, it may be centrifuged prior to application. The assay plates are then incubated at either 28° C. or 37° C. for 24 hours. Following incubation, the inhibition zones are measured. Effects on growth are also noted as to appearance. The compound is seen to effectively inhibit growth of the fungal organisms.

In view of the broad spectrum of activity, the compound of the present invention, either singly or as a mixture, is adaptable to being utilized in various applications of antifungal compositions. In such case, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compound may be admixed with a pharmaceutically acceptable carrier, the nature of which will depend on whether the composition is to be topical, parenteral or oral.

If said application is to be topical, the drug may be formulated in conventional creams and ointments such as white petrolatum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by mixing the component drugs with any of the usual pharmaceutical media, including for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricants such as calcium stearate, together with binders, disintegrating agents and the like. Water is the preferred liquid carrier for the compound of the invention.

These compositions are then administered in amounts sufficient to obtain the desired antifungal effect. For medical applications, the method comprises administering to a subject in need of treatment a therapeutically effective antifungal amount of the compounds. The appropriate dose will vary depending on age, severity, body weight and other conditions. For topical application, the compositions are applied directly to the area where control is desired. For internal administration, the composition may be applied by injection or may be administered orally.

For non-medical application, the product of the present invention, either alone or as a mixture, may be employed in compositions in an inert carrier which included finely divided dry or liquid diluents, extenders, fillers, conditioners and excipients, including various clays, diatomaceous earth, talc, and the like or water and various organic liquids such as lower alkanols, such as ethanol and isopropanol.

The following example illustrates the invention but is not to be construed as limiting the invention disclosed herein.

EXAMPLE I

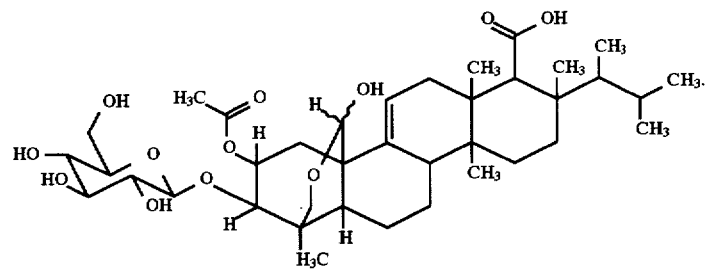

(I)

Isolation

A methyl ethyl ketone (MEK) extract (3.4 L) was concentrated to 110 ml, dried and partitioned with 800 ml hexane, 600 ml methanol and 100 ml 0.1% aq. TFA. The lower layer was then concentrated to dryness and partitioned with 50 ml methanol, 10 ml $H_2O$ and 50 ml hexane. The active component was located in the lower layer in both partitions.

An LH-20 separation was developed [$CH_2Cl_2$/hexanes/ MeOH (10:10:3)] and applied to a 940 ml whole broth extract portion of the active lower layer from the partitions. The rich cut was dried, reconstituted in $CH_3CN$ 0.1% TFA/$H_2O$ 0.1% TFA (1:1), and chromatographed on a 250×9.4 mm Zorbax RXC8 column at 2 ml/min using the conditions described in the following table:

| Time | | $H_2O$(0.1% TFA) | $CH_3CN$(0.1% TFA) |
|---|---|---|---|
| 0–20 minutes | Isocratic | 50% | 50% |
| 20–35 minutes | Gradient | 50% to 10% | 50% to 90% |
| 35–50 minutes | Isocratic | 10% | 90% |

The activity was located in fractions 24–30. 1.95 mg of the compound was obtained with an isolated titer of approximately 2 mg/L.

The following examples illustrate representative compositions containing Compound I

EXAMPLE A 1000 compressed tablets each containing 500 milligrams of Compound I are prepared from the following formulation:

| | Grams |
|---|---|
| Compound I | 500 |
| Starch | 750 |

| | Grams |
|---|---|
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

| | Grams |
|---|---|
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectible solution are prepared by conventional procedures from the following formulation:

| | |
|---|---|
| Dextrose | 12.5 grams |
| Water | 250 milliliters |
| Compound I | 400 milligrams |

The ingredients are blended and sterilized for use.

EXAMPLE D

An ointment suitable for topical application may be prepared by intimately dispersing 13 mg of Compound I in 1 g of commercially available polyethylene/hydrocarbon gel.

EXAMPLE E

An aerosol composition may be prepared having the following formulation (per canister):

| | |
|---|---|
| Compound I | 24 mg |
| Lecithin NF, liquid concentrate | 1.2 mg |
| Trichlorofluoromethane | 4.025 g |
| Dichlorodifluoromethane | 12.15 g |

What is claimed is:

1. A compound having the structure:

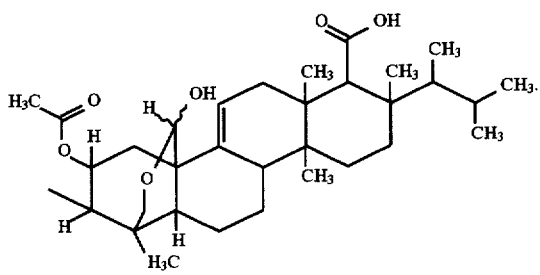
(I)

2. A method for controlling fungal growth which comprises administering to the site where growth is to be controlled, an antifungally effective amount of the compound of claim 1.

3. A method for combating fungal infections in mammals which comprises administering to a region of a mammal afflicted with said fungi a therapeutically effective amount of the compound of claim 1.

4. A process for producing the compound of claim 1 which comprises aerobically cultivating a culture of Hormonema sp., MF 6176, in a nutrient medium containing assimilable sources of carbon and nitrogen and isolating said compound therefrom.

5. An antifungal composition comprising the compound of claim 1 and an acceptable carrier therefor.

* * * * *